(12) United States Patent
Thompson et al.

(10) Patent No.: US 6,193,748 B1
(45) Date of Patent: Feb. 27, 2001

(54) OCCLUSION DEVICE

(75) Inventors: Paul J. Thompson, New Hope; Claude Clerc, Eden Prairie, both of MN (US)

(73) Assignee: Schneider (USA) INC, Maple Grove, MN (US)

( * ) Notice: Subject to any disclaimer, the term of this patent is extended or adjusted under 35 U.S.C. 154(b) by 0 days.

(21) Appl. No.: 09/332,284

(22) Filed: Jun. 11, 1999

Related U.S. Application Data

(63) Continuation of application No. 08/797,983, filed on Feb. 12, 1997, now Pat. No. 5,919,224.

(51) Int. Cl.[7] ............................................. A61F 2/00
(52) U.S. Cl. ............................................................ 623/1.3
(58) Field of Search ................................. 606/200, 198, 606/194; 623/1.13, 1.16, 1.2, 1.24, 1.3, 1.31, 1.49–1.54

(56) References Cited

U.S. PATENT DOCUMENTS

| 5,344,427 | * | 9/1994 | Cottenceau et al. | 606/200 |
|---|---|---|---|---|
| 5,375,612 | * | 12/1994 | Cottenceau et al. | 606/194 |
| 5,397,351 | * | 3/1995 | Pavcnik et al. | 623/11 |
| 5,527,338 | * | 6/1996 | Purdy | 606/200 |
| 5,618,301 | * | 4/1997 | Hauenstein et al. | 606/198 |
| 5,634,942 | * | 6/1997 | Chevillon et al. | 623/1 |
| 5,683,411 | * | 11/1997 | Kavteladze et al. | 606/200 |
| 5,709,704 | * | 1/1998 | Nott et al. | 606/200 |

* cited by examiner

*Primary Examiner*—Michael J. Milano
(74) *Attorney, Agent, or Firm*—Faegre & Benson LLP

(57) ABSTRACT

The present invention is an occlusion device adapted for implantation into a fluid flow-supporting body lumen. The occlusion device comprises a flexible support structure and a flexible fluid flow-occluding membrane that is positioned concentric with the flexible support structure. The support structure is formed from a plurality of interwoven filaments that form an axially flexible and radially compressible structure that, in its expanded state, engages the lumen. The membrane generally includes a constricted region and constriction means, such as a mechanical seal, for closing the membrane at one end. The membrane is formed from a plurality of filaments, and in one embodiment, the membrane filaments are tightly interbraided with the structure filaments to form the occlusion device. Alternatively, the membrane is separately fabricated of interwoven filaments, and is positioned either within the support structure or without the structure so as to surround the support structure.

3 Claims, 5 Drawing Sheets

ND DEVICE

REFERENCE TO RELATED APPLICATION

This application is a continuation of U.S. patent application Ser. No. 08/797,983, filed Feb. 12, 1997 now U.S. Pat. No. 5,919,224, and entitled "Medical Device Having a Constricted Region for Occluding Fluid Flow In a Body Lumen," the entire disclosure of which is incorporated by reference in its entirety for all purposes.

BACKGROUND OF THE INVENTION

1. Field of the Invention

The present invention relates generally to implantable, radially expandable medical devices for occluding fluid flow in a body lumen. In particular, the present invention is an occlusion device having an interwoven support structure and fluid flow-occluding membrane.

2. Description of the Related Art

Medical devices adapted for implantation in body lumens that support fluid flow are well known and commercially available. One such device is the self-expandable stent of the type disclosed in the Wallsten U.S. Pat. No. 4,655,771, which is expressly incorporated herein by reference in its entirety. Self-expanding stents can be used to treat vascular stenosis and to maintain openings in the urinary, biliary, esophageal, tracheal and bronchial tracts of a patient. Self-expanding stents of the type shown in the Wallsten patent are formed from a number of resilient filaments that are helically wound and interwoven to form a porous lattice. The stents assume a substantially tubular form in their unloaded or expanded state when they are not subjected to external forces. When subjected to inwardly-directed radial forces, the stents are forced into a reduced-radius and extended length form, known as the loaded or compressed state. A delivery device, such as a catheter, that retains the stent in its compressed state is used to deliver the stent to a treatment site through a lumen in a patient's body. After the stent is positioned at the treatment site, the delivery device is actuated to release the stent, thereby allowing the stent to self-expand and engage the body lumen. The delivery device is then detached from the stent and removed from the body.

Another type of implantable device is a vena cava filter. Vena cava filters are implanted in the vena cava that lead to a patient's heart in order to trap emboli in the fluid flow that would otherwise be carried into the heart and lungs. Vena cava filters can include a structure similar to the self-expanding stents described above, but act as a filter that traps large particles and emboli in the flow while allowing the remaining fluid flow to pass through the device.

It is sometimes desirable, however, to completely occlude a body lumen or stop fluid flow to a lumen that has been bypassed. By way of example, occlusion can be used to control internal bleeding, bypass a lumen, relieve the pressure created by an aneurysm in a lumen, or stop the flow of fluid to a tumor in a lumen. Because of their generally porous nature and substantially tubular expanded form, self-expanding stents are typically not used to occlude a fluid flow within a body lumen. Similarly, vena cava filters are specifically designed to filter and trap only emboli while allowing the remaining fluid flow in a lumen to pass through the filter, and thus are not typically used to occlude a lumen.

Implantable medical devices have been designed, however, to occlude fluid flow in a body lumen. One such device is a balloon that is carried to a treatment site by a catheter or other similar instrument. When positioned at the treatment site, the balloon is filled with a fluid, such as a polymerized resin, thereby occluding the fluid flow in the body lumen.

Another type of implantable occlusion device is a wire coil that is first linearly stretched and then positioned at a treatment site in the body lumen. Devices of this type are generally disclosed in the Ritchart et al. U.S. Pat. No. 4,994,069 and the Phelps et al. U.S. Pat. No. 5,522,822. The coil is delivered to a treatment site by a catheter. Upon being released from the catheter the coil assumes a randomly shaped mass that substantially fills the lumen. The coil can also be coated with fibers or a braided fibrous element to promote clotting of the fluid flow at the treatment site.

A continuing need exists, however, for implantable medical devices that will effectively occlude fluid flow in a body lumen. Occlusion devices exhibiting a relatively high degree of biocompatibility, that are efficient to manufacture, and that can be deployed using known techniques would be especially desirable.

SUMMARY OF THE INVENTION

The present invention is an improved medical device adapted for implantation into a body lumen. The device includes a support structure and a flexible fluid flow-occluding member. In one embodiment, the flexible fluid-flow occluding member is an interwoven membrane. At least a portion of the support structure is expandable from a reduced-diameter compressed state to a self-supporting and lumen-engaging expanded state. The flexible fluid flow-occluding membrane has at least a first tubular end that is concentrically oriented and circumferentially engaged with the support structure, and a constricted region. At least a portion of the membrane is expandable with the support structure from a reduced-diameter compressed state to an expanded state for occluding fluid flow through the body lumen when the support structure is in the lumen-engaging expanded state.

In a second embodiment, the support structure includes a plurality of elongate structural filaments that are interwoven. The support structure is radially self-expandable from a reduced-diameter compressed state to a self-supporting and lumen-engaging expanded state. The flexible fluid flow-occluding membrane includes polymeric filaments that are interbraided with the structural filaments. The membrane has a first tubular end that is co-extensive with at least a portion of the length of the support structure and a constricted region. The membrane is expandable with the support structure from a reduced-diameter compressed state to an expanded state for occluding fluid flow through the body lumen when the support structure is in the lumen-engaging expanded state.

In a third embodiment of the present invention, the support structure includes a plurality of elongate structural filaments that are interwoven. The support structure is radially self-expandable from a reduced-diameter compressed state to a self-supporting and lumen-engaging expanded state. The flexible fluid flow-occluding membrane includes polymeric filaments that are interbraided with the structural filaments. The membrane has a first tubular end that is co-extensive with at least a portion of the length of the support structure and a constricted region. The membrane is expandable with the support structure from a reduced-diameter compressed state to an expanded state for occluding fluid flow through the body lumen when the support structure is in the lumen-engaging expanded state. The constricted region of the membrane extends from the tubular end beyond the end of the support structure.

In a fourth embodiment of the present invention, the medical device includes a radially self-expandable support structure, a flexible fluid flow-occluding membrane, and constriction means for constricting a portion of the support structure and the membrane for occluding fluid flow through the body lumen. The support structure has first and second opposite ends and includes a plurality of elongate structural filaments that are interwoven. The support structure is expandable from a reduced-diameter compressed state to a self-supporting and lumen-engaging expanded state. The flexible fluid-flow occluding membrane includes polymeric filaments that are interwoven with the structural filaments. The membrane is coextensive with at least a portion of the length of the support structure.

In a fifth embodiment of the present invention, the medical device is comprised of a radially self-expandable support structure and a flexible fluid flow-occluding membrane. The support structure includes a plurality of elongated structural filaments that are interwoven. The support structure is expandable from a reduced-diameter compressed state to a self-supporting and lumen-engaging expanded state. The flexible fluid flow-occluding membrane has at least a first tubular end that is concentrically oriented and circumferentially engaged with the support structure and a constricted region. The membrane is expandable with the support structure from a reduced diameter compressed state to an expanded state for occluding fluid flow through the body lumen when the support structure is in the lumen-engaging expanded state.

DETAILED DESCRIPTION OF THE PREFERRED EMBODIMENTS

Figure 1:
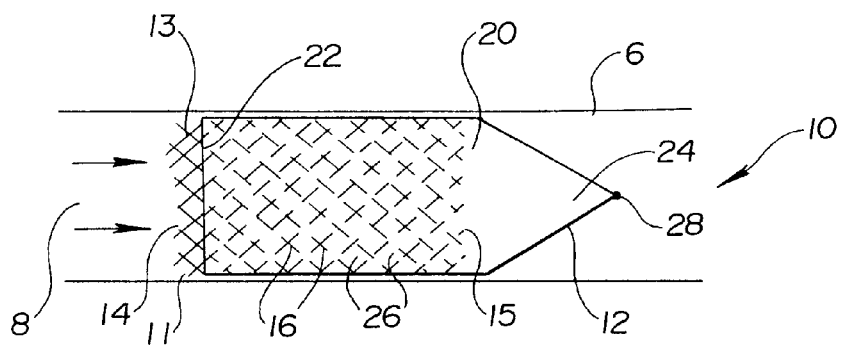
FIG. 1 is a side view of an interbraided occlusion device in accordance with the present invention in its expanded state and implanted in a body lumen.
Figure 2:
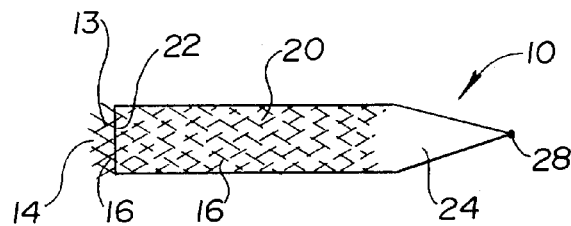
FIG. 2 is a side view of the occlusion device shown in FIG. 1 in its compressed state.

A first embodiment of an occlusion device 10 in accordance with the present invention is shown in FIGS. 1 and 2. Occlusion device 10 is substantially tubular, axially flexible, and radially compressible over at least a portion of the device, and is adapted to be implanted in a body lumen 6 that can support a fluid flow 8. As shown in FIG. 2, occlusion device 10 can be compressed in part or over the entire length of the device to a reduced-diameter state by subjecting the device to radially directed forces. When the entire length of occlusion device 10 is in this compressed state, the device can be inserted into body lumen 6 using conventional techniques and tools such as an insertion catheter (not shown). When released from the insertion catheter, the radial forces are removed from occlusion device 10, and it expands to the enlarged-diameter state shown in FIG. 1. When in this expanded state, occlusion device 10 engages body lumen 6, thereby anchoring the device in the lumen.

Occlusion device 10 is shown having an upstream end 11 that is open to accept fluid flow 8 into the device and a downstream end 12 that is closed to occlude the flow. Those skilled in the art, however, will recognize that occlusion device 10 can be reversed in fluid flow 8 so that the closed end of the device is the upstream end 11 while the open end of the device is the downstream end 12.

Occlusion device 10 is generally comprised of a support structure 13 and a fluid flow-occluding membrane 20. In the embodiment shown, support structure 13 is substantially tubular, axially flexible, and radially compressible over at least a portion of the structure, and has a first tubular end 14. Support structure 13 can be comprised of two sets of oppositely-directed elongate filaments 16 that are helically wound and interwoven to form a support structure 13 that is self-expandable. The sets of filaments 16 are interwoven in an over and under configuration, and intersect to form an open mesh construction. The first set of filaments 16 have a common direction of winding, are parallel and axially displaced relative to each other, and cross a second set of filaments 16 that are also parallel and axially displaced relative to each other, but have an opposite direction of winding.

Figure 6:
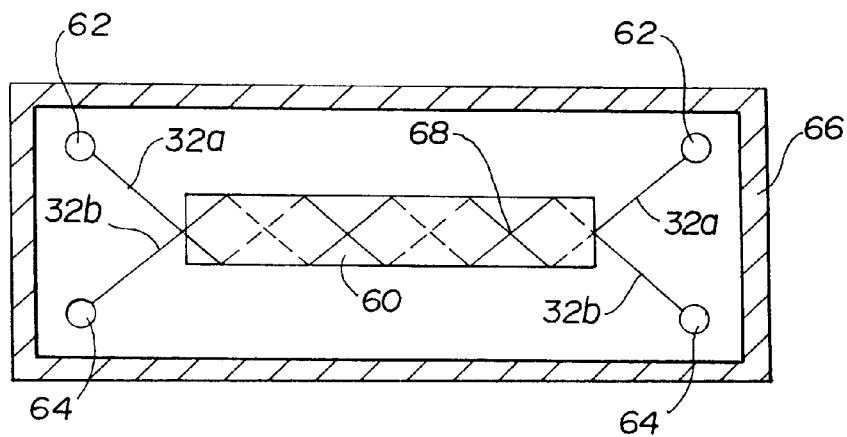
FIGS. 6–8 schematically illustrate a process for manufacturing the interbraided occlusion devices shown in FIGS. 1–5.

FIG. 6 shows a method for manufacturing a support structure 13 wherein two structural filaments 32a and 32b, one from each set of oppositely directed filaments, are wound about a mandrel 60 and supported by respective bobbins 62 and 64. While just filaments 32a and 32b are illustrated as a matter of convenience, it is to be appreciated that all of the structural filaments are wound about the mandrel and maintained together for shaping. The filaments are age-hardened within a furnace 66 in a vacuum or a protective atmosphere. Temperatures in furnace 66 range between about 350–1000° C., with the specific temperature depending upon the material used for the structural filaments. Filaments 32a and 32b overlie one another to form multiple intersections, one of which is indicated at 68. Bobbins, including 62 and 64, are set to tension their respective filaments during age-hardening. The appropriate duration for age-hardening varies with materials and dimensions, but can range from as brief as 30 seconds, to about 5 hours.

After age-hardening, the structural filaments are allowed to cool, whereupon each filament retains the helical shape as its nominal shape. In the context of elastic materials, "nominal shape" refers to the shape in a relaxed state, i.e. when under no external stress. The age-hardened filaments are highly resilient, i.e. deformable under external stress, but elastically return to the nominal shape when free of the external stress. In this manner, support structure 13 can be radially compressed into a reduced-radius, extended-length configuration suitable for delivery to a treatment site in body lumen 6. When released from this compressed state, support structure 13 will self-expand, thereby causing occlusion device 10 to engage body lumen 6.

Figure 14:
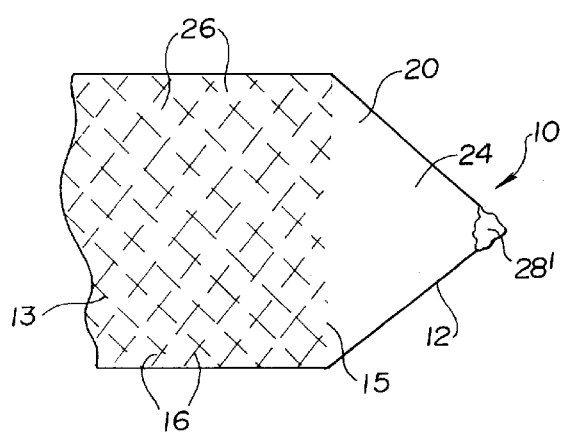
FIG. 14 is a detailed side view of a portion of the occlusion device shown in FIGS. 1 and 2 having a fusion seal.
Figure 15:
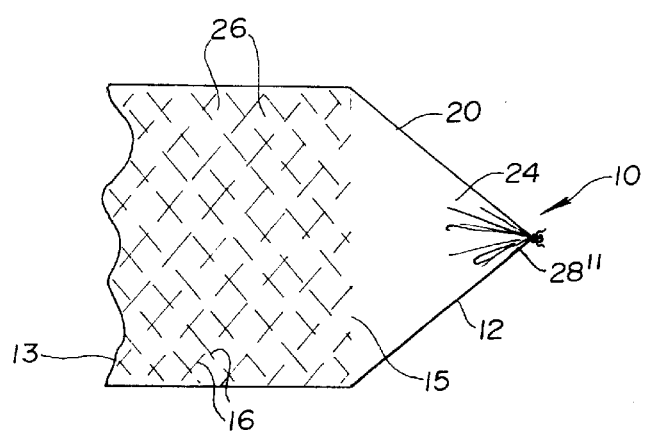
FIG. 15 is a detailed side view of a portion of the occlusion device shown in FIGS. 1 and 2 having a suture.

Fluid flow-occluding membrane 20 has a first tubular end 22 that is concentrically oriented and circumferentially engages support structure 13. Membrane 20 further includes at least one constricted region 24 that operates to occlude fluid flow 8 in lumen 6, and membrane 20 is expandable along with support structure 13 from the compressed state to the expanded state of the occlusion device 10. Membrane 20 can be closed at constricted region 24 by any of a number of constriction techniques, such as mechanical seal 28, in order to occlude fluid flow. Those skilled in the art will recognize that other constriction techniques, such as a sealing member, a fusion seal 28' as is shown in FIG. 14, or a suture 28" as is shown in FIG. 15, can also be used.

Figure 5:
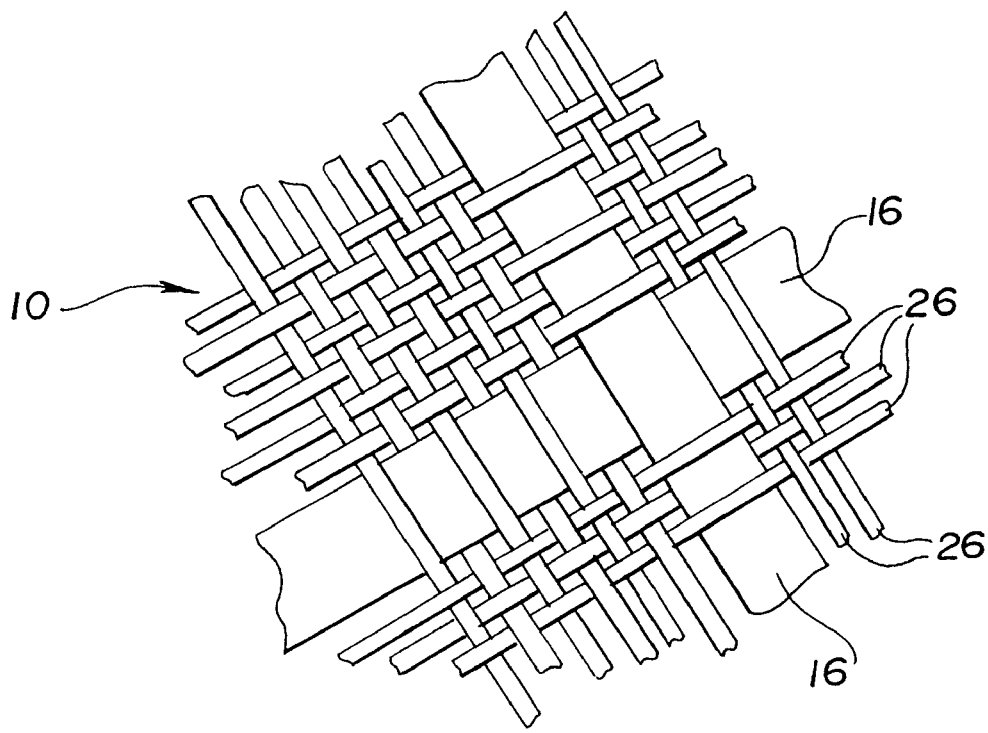
FIG. 5 is a detailed side view of a portion of an interbraided occlusion device showing the interbraided filaments of the device.
Figure 7:
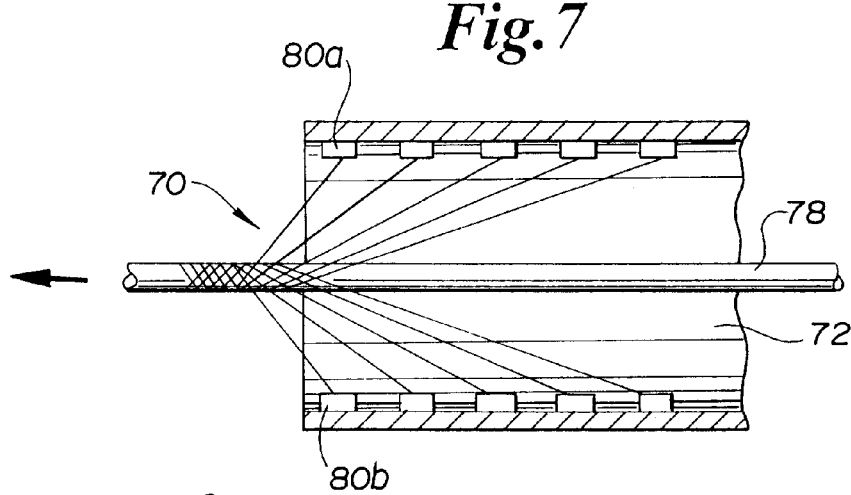
Figure 8:
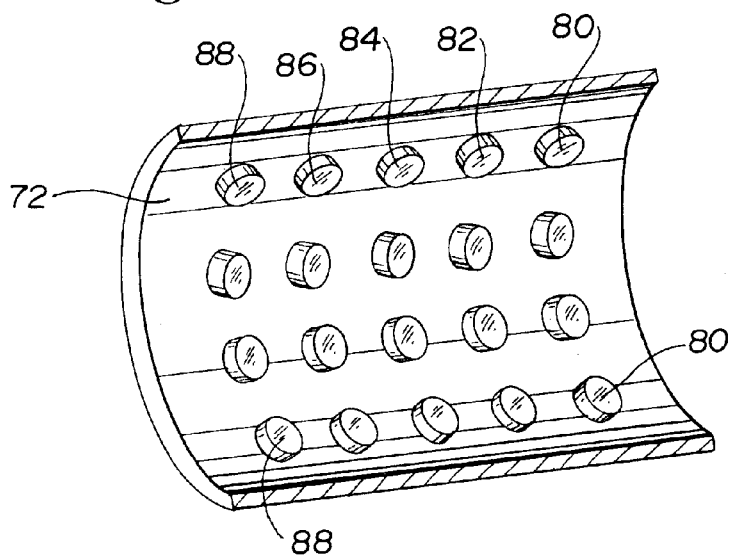

In the embodiment shown in FIGS. 1 and 2, membrane 20 includes a plurality of polymeric filaments 26 that, as shown in greater detail in FIG. 5, are interbraided with support structure filaments 16 in forming occlusion device 10. FIGS. 7 and 8 schematically illustrate a method for interbraiding membrane filaments with structural filaments. FIG. 7 shows a braiding apparatus 70 including a cylindrical carrier assembly 72 including several annular arrays of bobbins, two of the bobbins being indicated at 80a and 80b. The apparatus further includes a mandrel 78, centered within the cylindrical assembly and movable longitudinally relative to the assembly as indicated by the arrow.

FIG. 8 illustrates part of a carrier assembly 72 in greater detail, to reveal five annular arrays or sets of carrier bobbins indicated at 80, 82, 84, 86, and 88. The sets are coaxial and axially spaced apart, each including forty-eight bobbins, twenty-four bobbins for respective clockwise and counter-clockwise windings about mandrel 78. While those skilled in the art are acquainted with the use of braiding machinery, it is emphasized here that braiding apparatus 70 is configured as described in detail in the commonly assigned P. Thompson U.S. patent applications, Ser. Nos. 08/640,091 and 08/640,062 entitled "Three-Dimensional Braided Covered Stent" and entitled "Braided Composite Prosthesis," both of which are expressly incorporated herein by reference in their entirety. Suitable braiding machinery is available from Albany International Research Company of Mansfield, Mass.

Support structure filaments 16 and membrane filaments 26 can be tightly interwoven so that membrane 20 is generally non-porous in order to occlude fluid flow. Membrane filaments 26 can also be formed from a thrombogenic material in order to promote clotting of fluid flow 8 and thereby occlude the fluid flow. The resulting structure will preferably have a porosity of less than 5,000 ml/cm²/min at 120 mmHg. More preferred are porosities of between about 100 and 3,000 ml/cm²/min, and even more preferably, between about 300 and 2,000 ml/cm²/min at 120 mmHg.

In the interbraided occlusion device 10 shown in FIGS. 1 and 2, first tubular end 14 of support structure 12 extends beyond first tubular end 22 of membrane 20, and the constricted region 24 of membrane 20 extends beyond a second tubular end 15 of support structure 13. The individual membrane fibers 26 of membrane 20 are drawn together in the constricted region 24 and sealed together with mechanical seal 28.

Figure 3:
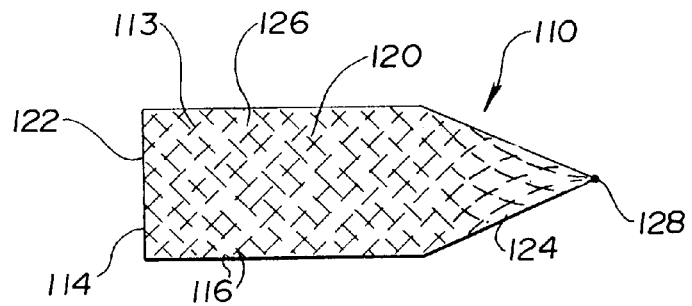
FIG. 3 is a side view of a second embodiment of an interbraided occlusion device in accordance with the present invention.

FIG. 3 shows a second embodiment of an interbraided occlusion device 110 in its expanded state. Features of occlusion device 110 that correspond to features of occlusion device 10 shown in FIGS. 1 and 2 and described above are designated with corresponding reference numbers that are preceded by the prefix "1." In this embodiment, support structure filaments 116 and membrane filaments 126 are interbraided throughout the entire length of occlusion device 110. Mechanical seal 128 compresses both support structure 112 and membrane 120 at the constricted region 124, thereby closing occlusion device 110 and occluding fluid flow through the device.

Figure 4:
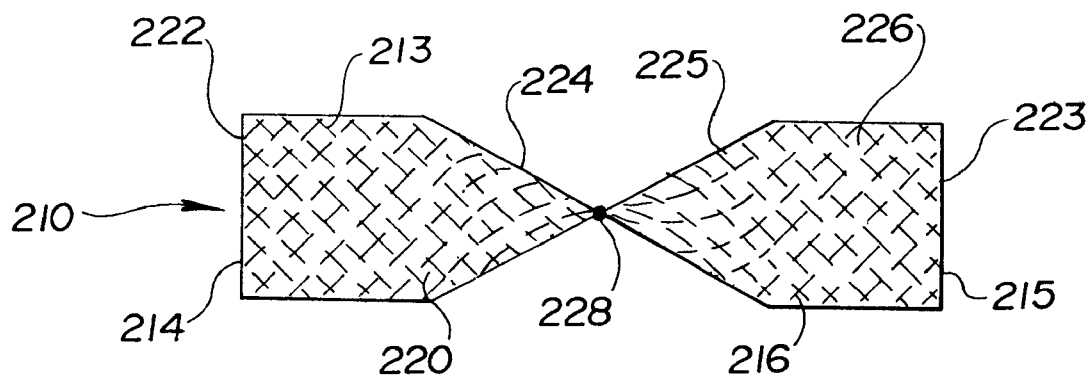
FIG. 4 is a side view of a third embodiment of an interbraided occlusion device in accordance with the present invention.

FIG. 4 shows a third embodiment of an interbraided occlusion device 210 in its expanded state. Features of occlusion device 210 that correspond to features of occlusion device 10 shown in FIGS. 1 and 2 and described above are designated with corresponding reference numbers that are preceded by the prefix "2." Support structure 213 includes first and second tubular ends 214 and 215, respectively, and fluid flow-occluding membrane 220 includes first and second tubular ends 222 and 223, respectively. In this embodiment, support structure filaments 216 and membrane filaments 226 are interbraided throughout the entire length of occlusion device 210, and the respective first and second ends of structure 213 and membrane 220 are thus concentric and substantially coextensive. Mechanical seal 228 is positioned between the first and second tubular ends of the occlusion device 210, and constricts both the support structure 213 and the membrane 220 in order to occlude fluid flow in a body lumen. Support structure 213 and membrane 220 radially expand in the areas adjacent mechanical seal 228 to form first and second constricted regions 224 and 225.

Figure 9:
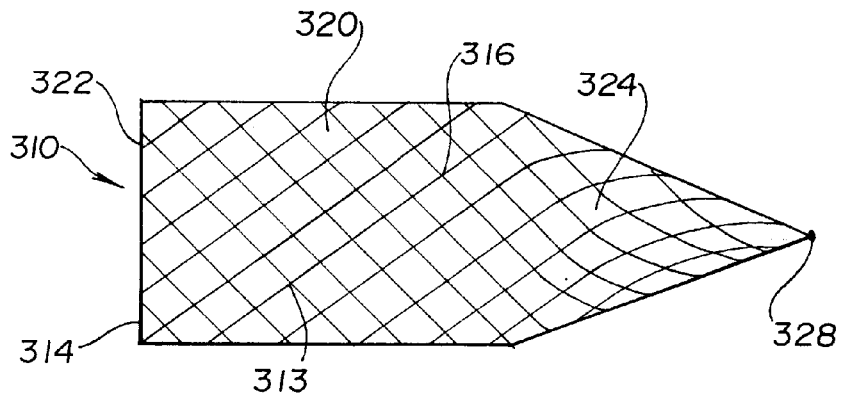
FIG. 9 is a side view of a sheath occlusion device in accordance with the present invention.
Figure 10:
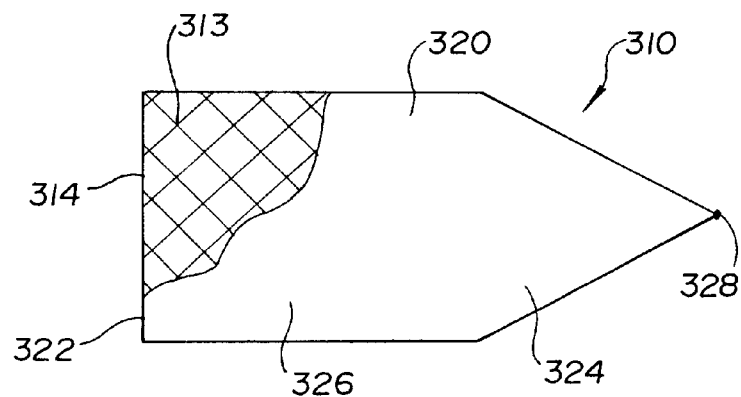
FIG. 10 is a side view of the sheath occlusion device shown in FIG. 9 with portions removed to show the membrane surrounding the support structure of the device.

FIGS. 9 and 10 show a sheath occlusion device 310 in accordance with the present invention. Sheath occlusion device 310 is comprised of support structure 313 and a separately fabricated fluid flow-occluding membrane 320. Support structure 313 can be comprised of a plurality of interbraided elongate filaments 316, and can be manufactured using the method for manufacturing support structure 13 described above and shown in FIG. 6. Membrane 320 circumferentially engages support structure 313, and in the embodiment shown in FIG. 9, membrane 320 is positioned within support structure 313. In this manner, support structure 313 acts as a "sheath" that covers membrane 320. Alternatively, as in the embodiment shown in FIG. 10, membrane 320 can encompass support structure 313, thereby acting as a sheath that covers structure 313.

Membrane 320 can be formed from a plurality of filaments 326 that are either tightly interwoven to occlude fluid flow, or are thrombogenic in order to promote clotting of the fluid flow, and thereby occlude the flow. Alternatively, membrane 320 can be formed from a sheet of flexible material that is substantially non-porous, is thrombogenic, or is covered with a non-porous coating in order to occlude fluid flow.

The sheath occlusion device 310 shown in FIGS. 9 and 10 includes a first tubular end 314 of support structure 313 and a first tubular end 322 of membrane 320 that are concentric and substantially coextensive, and support structure 313 extends the entire length of membrane 320. Membrane 320 and support structure 313 of occlusion device 310 are separately fabricated, and membrane 320 engages structure 313 using conventional techniques, such as adhesive or thread stitching. Mechanical seal 328 closes the support structure 313 and membrane 320 at the constricted region 324, thereby occluding fluid flow.

Figure 11:
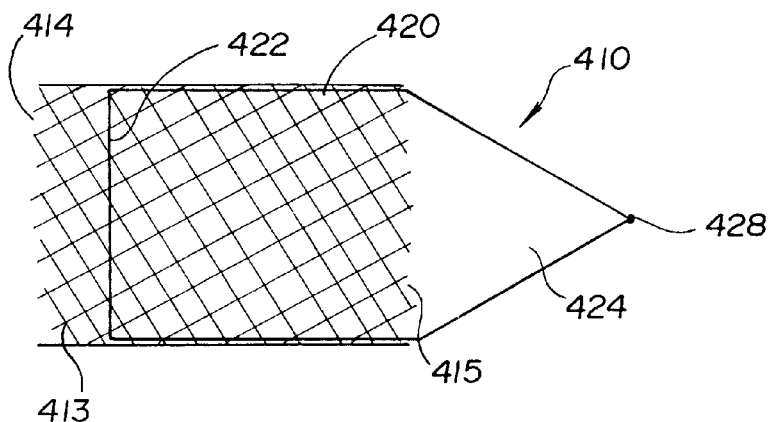
FIG. 11 is a side view of a second embodiment of a sheath occlusion device in accordance with the present invention.

FIG. 11 shows a second embodiment of a sheath occlusion device 410 in accordance with the present invention. Features of occlusion device 410 that correspond to features of occlusion device 310 shown in FIGS. 9 and 10 and described above are designated with "400" series reference numbers as opposed to the "300" series used in FIGS. 9 and 10. Sheath occlusion device 410 includes a support structure 413 and membrane 420 that are separately fabricated, and a first tubular end 414 of support structure 413 extends beyond a first tubular end 422 of membrane 420. Support structure 413 thus acts as a sheath that surrounds a portion of membrane 420. A constricted region 424 of membrane 420 extends beyond a second tubular end 415 of support structure 413, and is closed at constricted region 424 with mechanical seal 428.

Figure 12:
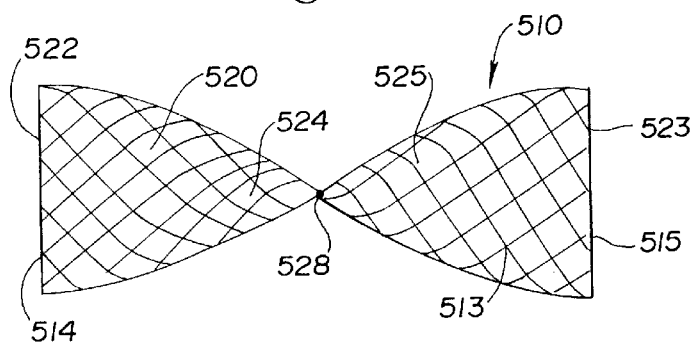
FIG. 12 is a side view of a third embodiment of a sheath occlusion device in accordance with the present invention.

FIG. 12 shows a third embodiment of a sheath occlusion device 510. Features of occlusion device 510 that correspond to features of occlusion device 310 shown in FIGS. 9 and 10 and described above are designated with "500" series reference numbers as opposed to the "300" series used in FIGS. 9 and 10. Sheath occlusion device 510 includes a support structure 513 and membrane 520 that are separately fabricated. First tubular ends 514 and 522 of support structure 513 and membrane 520, respectively, are concentric and substantially coextensive, as are second tubular ends 515 and 523 of the structure and the membrane. Mechanical seal 528 is positioned between the first and second ends of the device, and engages both support structure 513 and membrane 520 at the constricted region 524. Due to the self-expanding nature of support structure 513, the areas adjacent mechanical seal 528 expand, thereby creating a second constricted region 525. While occlusion device 510 is shown with membrane 520 positioned within support structure 513, those skilled in the art will recognize that membrane 520 can alternatively surround support structure 513 without departing from the spirit and scope of the invention.

Figure 13:
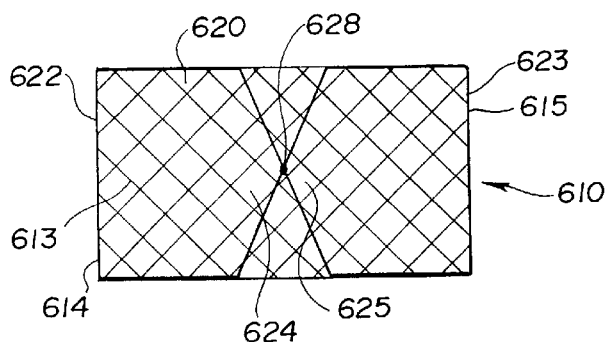
FIG. 13 is a side view of a fourth embodiment of a sheath occlusion device in accordance with the present invention.

FIG. 13 shows a fourth embodiment of a sheath occlusion device 610. Features of occlusion device 610 that correspond to features of occlusion device 310 shown in FIGS. 9 and 10 and described above are designated with "600" series reference numbers as opposed to the "300" series used in FIGS. 9 and 10. A separately fabricated membrane 620 is positioned within and engages support structure 613. In this embodiment, mechanical seal 628 is also positioned within support structure 613, and thus closes only membrane 620 at the constricted region 624. Because membrane 620 engages support structure 613, membrane 620 expands in the areas adjacent mechanical seal 628, thereby creating a second constricted region 625.

The elongate filaments of the support structures described above can be formed from a metal or other resilient material, including Elgiloy® alloy (available from Carpenter Technology Corporation of Reading, Pa.), Phynox® alloy (available from Metal Imphy of Imphy, France), 316 stainless steel and MP35N alloy (both of which are available from Carpenter Technology Corporation and Latrobe Steel Company of Latrobe, Pa.), and superelastic Nitinol nickel-titanium alloy (available from Shape Memory Applications of Santa Clara, Calif.).

The fluid flow-occluding membranes of the present invention described above generally have a high degree of compliance, which may or may not include elasticity. These membranes can be formed from a plurality of filaments that are either tightly woven to occlude fluid flow, or are thrombogenic to promote clotting of the fluid flow, and thereby occlude the flow. Suitable materials for the plurality of filaments include polyethylene and polyethylene terephthalate. One suitable high molecular weight polyethylene that can be used for the filaments is sold under the brand name "Spectra". Alternatively, these membranes can be formed from a sheet of flexible material that is non-porous, is thrombogenic, or is covered with a non-porous coating to occlude fluid flow. Suitable materials for a sheet of flexible material used to form the membranes include silicone, polyurethane, polycarbonate urethane, polytetrafluoroethylene, or expanded polytetrafluoroethylene.

The occlusion device described above has many advantages. The device exhibits a relatively high degree of biocompatibility. The support structure securely engages the device in a body lumen while the membrane effectively occludes fluid flow in the lumen. In addition, the occlusion device can be deployed using conventional insertion techniques and tools, such as an insertion catheter. The present invention is also efficient to manufacture.

Although the present invention has been described with reference to preferred embodiments, those skilled in the art will recognize that changes can be made in form and detail without departing from the spirit and scope of the invention.

What is claimed is:

1. A medical device adapted for implantation into a body lumen having a tubular interior surface, including:

a support structure of which at least a tubular portion is expandable from a reduced-diameter compressed state to a self-supporting and lumen-engaging expanded state, the tubular portion for engaging the tubular interior surface of the lumen in the expanded state; and a flexible fluid flow-occluding membrane having an edge portion circumferentially engaged with the support structure and having a constricted occluding region extending between the edge portion, the membrane being expandable with the support structure from a reduced diameter compressed state to an expanded state at which the support structure causes the edge portion of the membrane to be engaged with the interior surface of the lumen, for occluding fluid flow and substantially preventing fluid flow through the body lumen when the support structure is in the lumen-engaging expanded state.

2. The medical device of claim 1, wherein the support structure includes a plurality of elongate structural filaments that are interwoven.

3. The medical device of claim 2, wherein the fluid flow-occluding membrane includes a plurality of polymeric filaments interwoven with the structural filaments.

* * * * *